Sept. 24, 1963 E. GOULD Plant Pat. 2,285
APPLE TREE
Filed Dec. 26, 1961
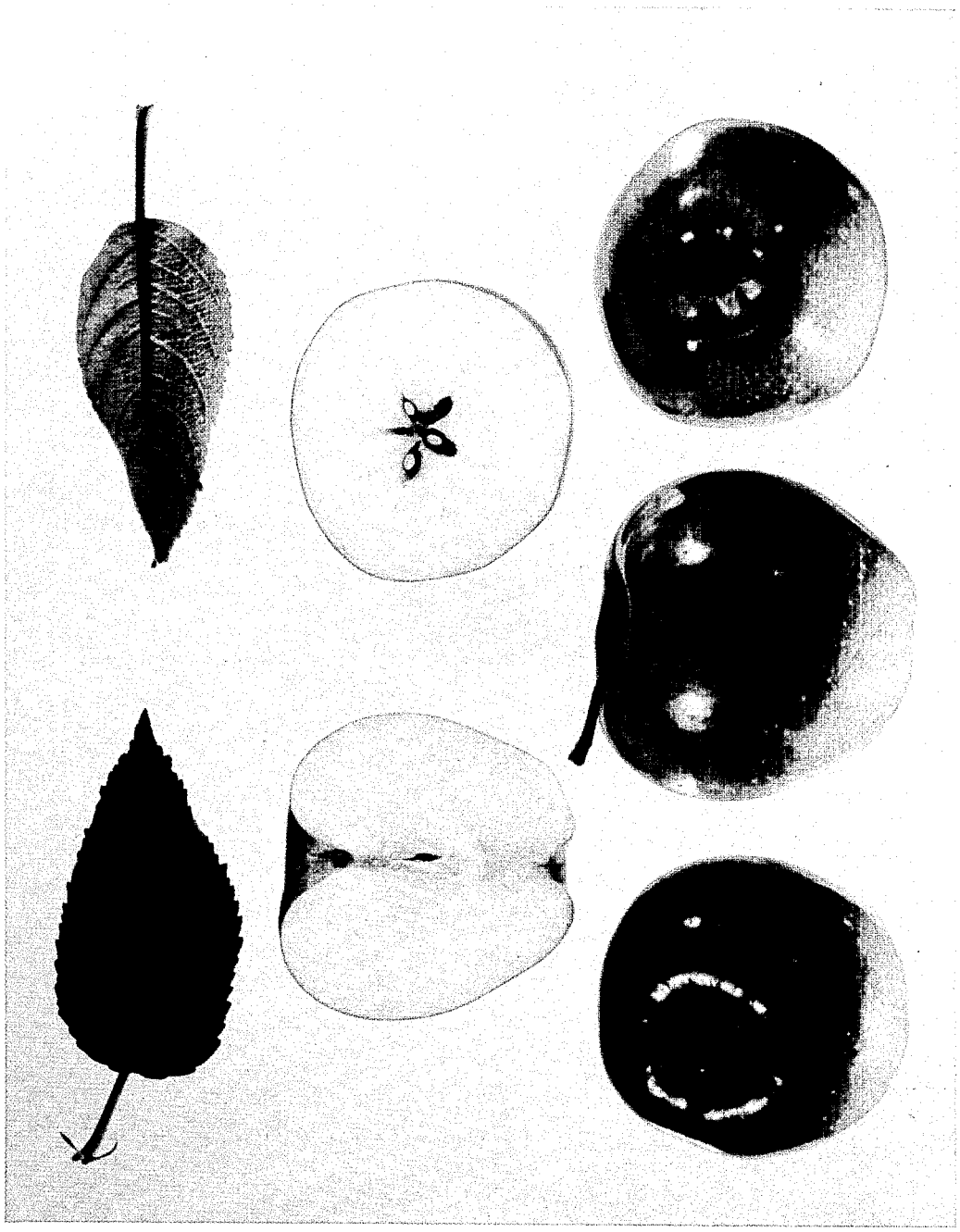
INVENTOR
Edwin Gould
BY Robb & Robb
ATTORNEYS United States Patent Office Plant Pat. 2,285
Patented Sept. 24, 1963

2,285
APPLE TREE

Edwin Gould, Kearneysville, W. Va., assignor to Edward W. Miller, Romney, and Henry W. Miller, Jr., Paw Paw, W. Va.

Filed Dec. 26, 1961, Ser. No. 162,295
1 Claim. (Cl. Plt.—35)

The present invention relates to a new and distinct variety of apple tree which was discovered by me as a limb sport during the course of my supervision of an orchard near Martinsburg, West Virginia.

At the time of my initial discovery of the new variety aforesaid, I was engaged in making a personal orchard inspection on the property referred to above, and during the course thereof, my attention was attracted to a particular tree amongst those of the variety "Red Delicious" (unpatented) being grown in said orchard, and which appeared to be bearing fruit that was noticeably different from the normal fruit of the variety "Red Delicious," as evidenced by a streak of red color through the tree as attributed to an unusually early coloring of the fruit of the "Red Delicious" tree. A closer inspection of this particular tree showed that the fruit on one limb had acquired a much earlier red coloring than any other fruit on the same tree. Still further examination established that the tree had sported, and I accordingly took prompt steps to preserve the sport and have it asexually reproduced for the purpose of determining whether the early coloring characteristics were fixed and transmissible by asexual reproduction.

My continued observations of the original sport and of the progeny thereof produced by both budding and grafting, as performed under my direction at Paw Paw, West Virginia, conclusively showed that the coloring of the fruit of the new variety was not only a characteristic of unusual earliness, but in addition represented a more intense, solid red color and of unusual uniformity throughout the tree, combined with good color retention throughout the ripening season, without any tendency to "buckskin" during hot weather, particularly near harvest time, and combined still further with the superior good eating qualities of the fruit comparable to the fruit of the parent variety "Red Delicious." The fruit of no other recognized strain carries this same quality of intense early bright pigmentation, with all other characteristics being comparable to the parent strain.

Together, the aforementioned characteristics represent a unique and commercially valuable combination which definitely differentiates my new sport from the variety "Red Delicious," as well as from all other varieties of which I am aware.

The accompanying drawing shows typical specimens of the foliage and fruit of my new variety, with certain of the fruit specimens being shown in cross section, and with certain of the foliage specimens showing the upper and under surfaces, respectively, thereof, all as depicted in color as nearly true as it is possible to make the same in a color illustration of this character.

The following is a detailed description of the new variety, with color terminology in accordance with the Nickerson Color Fan, as published by Munsell Color Company, Inc., of Baltimore, Maryland, except where general color terms of ordinary dictionary significance are obvious, said description being based upon observations made from specimens grown at Paw Paw, West Virginia:

Dates of first and last pickings: About September 12 and about September 25, respectively.

Tree: Large; vigorous; upright; tall; fairly open; rapid growing; hardy; very productive; regular bearer.

*Trunk.*—Stocky; smooth.

*Branches.*—Thick; smooth; much-branched. Color—brown. Lenticels—numerous; from medium to small size.

*Leaves.*—Medium size; medium thickness; taper-pointed. Shape—obovate. Length—from about 3 inches to about 4 inches. Width—from about 1½ inches to about 2 inches. Color—near Strong Green, Plate 5G 4/7. Margin—finely serrate. Petiole—medium length (from about ¾ inch to about 1 inch); medium thickness.

Flowers: Medium late (first bloom about May 1st and full bloom about May 5th); medium size. Color—pinkish.

Fruit:

*Maturity when described.*—Eating ripe (date about October 1).

*Size.*—Uniform. Axial diameter—from about 3½ inches to about 4 inches. Transverse diameter—from about 3¼ inches to about 3¾ inches.

*Form.*—Uniform; symmetrical; regular; oblate; conical.

*Cavity.*—Symmetrical; abrupt at base; depth about ½ inch; breadth about 1 inch. Markings—none.

*Basin.*—Unsymmetrical; flaring; furrowed; undulate; crowned; depth about ⅜ inch; breadth about 1 inch.

*Stem.*—Medium caliper; length from about 1 inch to about 1½ inches; bracts wanting.

*Calyx.*—Closed; segments persistent; broadly lanceolate; acute; about 5/16 inch long; approximate at base; prostrate; reflexed from base at apex; both outer and inner surfaces pubescent.

*Eye.*—Small; partially closed.

*Skin.*—Medium thickness; medium toughness; smooth; glossy; waxed. Dots—conspicuous; many; small; even; circular; color—white; distribution—all over. Ground color—straw yellow. Color markings—blushed; bright; color—smooth, velvety, solid red, near Dark Red, Plate 2.5R 3/7.

*Bloom.*—Moderate.

*Scarfskin.*—Wanting.

*General color effect.*—Deep solid red.

*Flesh.*—Juicy. Color—white. Texture—firm; fine; crisp. Flavor—mild; sprightly. Aroma—slight. Quality—best.

*Core.*—Median; distinct in cross section. Bundle area—medium size; cordate; symmetrical at base; acute at base; in bundles opposite and alternate with cell. Halves of core—equal. Bundles—inconspicuous; in one whorl; color—Dark Greenish Yellow, Plate 7.5Y 6/7. Core lines—clasping. Carpellary area—distinct; medium size. Calyx tube—glabrous toward base; broadly obconic; urn-shaped; depth of tube to shoulder—about 3/16 inch; entire depth—about ½ inch. Styles—present; distinct; pubescent. Stamens—in one distinct whorl; marginal. Axillary cavity—present. Seed cells—axile; open; cell walls—distinct; thick; tough; length—about ½ inch; breadth—about ¼ inch; longitudinal section—broadly oval; acute at apex; surface—fissured; cross section—broad.

Seeds:

*Number.*—Usually about 10; average of usually 2 seeds per cell. Length—about ¼ inch. Breadth—about ⅛ inch.

*Form.*—Obtuse.

*Color.*—Moderate Brown, Plate 5YR 3/3

Use: Market; dessert.

Keeping quality: Good; about 60 days in ordinary storage.

I claim:

A new and distinct variety of apple tree, substantially as herein shown and described, characterized particularly as to novelty by the unique combination of an unusually early, intense, solid red coloring of the fruit and uniformity of the color throughout the tree, good color retention without tendency to "buckskin" during hot weather, particularly near harvest time, and good eating qualities of the fruit comparable to the fruit of the parent variety "Red Delicious" (unpatented).

No references cited.